(12) United States Patent
Stefanski et al.

(10) Patent No.: US 11,596,743 B2
(45) Date of Patent: Mar. 7, 2023

(54) CLUTCH ASSEMBLY WITH A BLOCKING SYSTEM FOR A MEDICAL INJECTION DEVICE

(71) Applicant: NEMERA SZCZECIN SPOLKA E OGRANICZONA ODPOWIEDZIALNOSCIA, Szczecin (PL)

(72) Inventors: Adam Stefanski, Gniezno (PL); Alberto Lozano Platonoff, Szczecin (PL)

(73) Assignee: NEMERA SZCZECIN SPOLKA Z OGRANICZONA ODPOWIEDZIALNOSCIA, Szczecin (PL)

( * ) Notice: Subject to any disclaimer, the term of this patent is extended or adjusted under 35 U.S.C. 154(b) by 458 days.

(21) Appl. No.: 16/631,307

(22) PCT Filed: Mar. 20, 2018

(86) PCT No.: PCT/IB2018/051857
§ 371 (c)(1),
(2) Date: Jan. 15, 2020

(87) PCT Pub. No.: WO2018/207034
PCT Pub. Date: Nov. 15, 2018

(65) Prior Publication Data
US 2020/0147308 A1    May 14, 2020

(30) Foreign Application Priority Data
Jul. 18, 2017   (PL) ......................................... 422256

(51) Int. Cl.
*A61M 5/315*    (2006.01)
*A61M 5/20*    (2006.01)
(Continued)

(52) U.S. Cl.
CPC .......... *A61M 5/24* (2013.01); *A61M 5/31551* (2013.01); *A61M 5/2033* (2013.01);
(Continued)

(58) Field of Classification Search
CPC ................ A61M 5/24; A61M 5/31551; A61M 5/31541; A61M 5/31585; A61M 5/3155;
(Continued)

(56) References Cited

U.S. PATENT DOCUMENTS

| 533,575 A | 2/1895 | Wilkens |
| 2,444,570 A | 8/1946 | Lawrence et al. |

(Continued)

FOREIGN PATENT DOCUMENTS

| CN | 203017504 U | 6/2013 |
| CN | 104159628 A | 11/2014 |

(Continued)

*Primary Examiner* — Tasnim Mehjabin Ahmed
(74) *Attorney, Agent, or Firm* — Browdy and Neimark, PLLC

(57) ABSTRACT

A clutch assembly with a blocking system for a medical injection device, in which a first ratchet sleeve (3) is mounted on the clutch sleeve (2), the first ratchet sleeve (3) being rotatable in two directions and cooperating with a second ratchet sleeve (4) which is mounted on the first ratchet sleeve (3), the second ratchet sleeve (4) being rotatable only in one direction, the housing (1) has an internal toothed ring (1.1), the first ratchet sleeve (3) has at least one ratchet (3.1), and the second ratchet sleeve (4) has an internal toothed ring (4.1) and at least one ratchet (4.2). The second ratchet sleeve (4) and the housing (1) have blocking means (4.3, 1.2) for preventing the arming of the device when an insufficient volume of the medicament remains in the container, by blocking the rotation of the second ratchet sleeve (4) in relation to the housing (1).

10 Claims, 2 Drawing Sheets

(51) Int. Cl.
*A61M 5/24* (2006.01)
*A61M 5/31* (2006.01)

(52) U.S. Cl.
CPC ..... *A61M 5/31541* (2013.01); *A61M 5/31585* (2013.01); *A61M 2005/3126* (2013.01)

(58) Field of Classification Search
CPC .......... A61M 5/31528; A61M 5/31568; A61M 5/2033; A61M 5/20; A61M 2005/3126; A61M 2005/2073; A61M 3/00
See application file for complete search history.

(56) References Cited

U.S. PATENT DOCUMENTS

| | | | |
|---|---|---|---|
| 2,717,597 | A | 12/1952 | Hein, Jr. |
| 4,470,317 | A | 9/1984 | Sabloewski et al. |
| 4,498,904 | A | 9/1985 | Turner et al. |
| 5,304,152 | A | 4/1994 | Sams et al. |
| 5,320,609 | A | 6/1994 | Haber et al. |
| 5,480,387 | A | 1/1996 | Gabriel et al. |
| 5,505,704 | A | 4/1996 | Pawelka |
| 5,626,566 | A | 5/1997 | Peterson |
| 5,674,204 | A | 10/1997 | Chanoch et al. |
| 5,688,251 | A | 11/1997 | Chanoch et al. |
| 6,083,197 | A | 7/2000 | Umbaugh |
| 6,221,046 | B1 | 4/2001 | Burroughs et al. |
| 6,899,698 | B2 | 5/2005 | Sams et al. |
| 7,896,850 | B2 | 3/2011 | Kronestedt |
| 7,918,833 | B2 | 3/2011 | Veasey |
| 8,357,120 | B2 | 1/2013 | Petersen |
| 8,376,993 | B2 | 2/2013 | Cox et al. |
| 8,512,297 | B2 | 8/2013 | Veasey |
| 8,603,044 | B2 | 12/2013 | Veasey |
| 8,608,708 | B2 | 12/2013 | Cowe |
| 8,617,109 | B2 | 12/2013 | Kronestedt et al. |
| 8,663,167 | B2 | 3/2014 | Bartha |
| 8,679,069 | B2 | 3/2014 | Veasey |
| 8,684,969 | B2 | 4/2014 | Moller |
| 8,915,889 | B2 | 12/2014 | Cox et al. |
| 8,920,383 | B2 | 12/2014 | Enggaard |
| 8,992,486 | B2 | 3/2015 | Veasey |
| 9,011,386 | B2 | 4/2015 | Kronestedt |
| 9,011,391 | B2 | 4/2015 | Veasey |
| 9,022,994 | B2 | 5/2015 | Moser |
| 9,044,548 | B2 | 6/2015 | Miller |
| 9,095,658 | B2 | 8/2015 | Wieselblad |
| 9,138,542 | B2 | 9/2015 | Smith |
| 9,205,195 | B2 | 12/2015 | Burren et al. |
| 9,233,211 | B2 | 1/2016 | Veasey |
| 9,408,979 | B2 | 8/2016 | Veasey |
| 9,415,165 | B2 | 8/2016 | Cowe |
| 9,526,844 | B2 | 12/2016 | Veasey |
| 9,561,333 | B2 | 2/2017 | Cox et al. |
| 9,566,386 | B2 | 2/2017 | Stefanski |
| 9,623,190 | B2 | 4/2017 | Veasey |
| 9,687,611 | B2 | 6/2017 | Moeller |
| 9,775,954 | B2 | 10/2017 | Veasey |
| 2002/0052578 | A1* | 5/2002 | Moller .............. A61M 5/31541 604/208 |
| 2004/0059299 | A1 | 5/2004 | Moller |
| 2006/0276753 | A1 | 12/2006 | Kronestedt |
| 2007/0016143 | A1 | 1/2007 | Miller et al. |
| 2007/0129687 | A1 | 6/2007 | Marshall |
| 2009/0054851 | A1 | 2/2009 | Radmer |
| 2009/0227955 | A1 | 9/2009 | Hirschel |
| 2009/0247951 | A1* | 10/2009 | Kohlbrenner .......... A61M 5/20 604/134 |
| 2009/0275916 | A1 | 11/2009 | Harms |
| 2010/0298781 | A1 | 11/2010 | Hogdahl |
| 2011/0034878 | A1 | 2/2011 | Radmer |
| 2012/0283647 | A1 | 11/2012 | Cronenberg |
| 2015/0080812 | A1 | 3/2015 | Enggaard |
| 2015/0265776 | A1 | 9/2015 | van der Beek |
| 2015/0290397 | A1 | 10/2015 | Wieselblad |
| 2015/0367078 | A1* | 12/2015 | Pedersen .......... A61M 5/31553 74/530 |
| 2016/0022919 | A1 | 1/2016 | Cammish et al. |
| 2016/0051770 | A1 | 2/2016 | Jones |
| 2016/0121052 | A1 | 5/2016 | Burren |
| 2016/0136358 | A1 | 5/2016 | Oakley |
| 2016/0151577 | A1 | 6/2016 | Newton |
| 2016/0317752 | A1 | 11/2016 | Cowe |
| 2017/0087307 | A1 | 3/2017 | Cox |
| 2017/0100547 | A1 | 4/2017 | Stefanski |
| 2017/0119973 | A1 | 5/2017 | Roervig |
| 2017/0224924 | A1 | 8/2017 | Christensen |

FOREIGN PATENT DOCUMENTS

| | | |
|---|---|---|
| DE | 3609555 | 9/1987 |
| EP | 0338806 A2 | 10/1989 |
| EP | 0295075 | 12/1991 |
| EP | 0937471 | 9/2005 |
| EP | 1728529 | 7/2008 |
| EP | 1819382 | 10/2009 |
| EP | 2274030 A1 | 1/2011 |
| EP | 1909870 | 3/2011 |
| EP | 2351591 A1 | 8/2011 |
| EP | 2364742 | 9/2011 |
| EP | 1694387 | 7/2012 |
| EP | 2484395 | 8/2012 |
| EP | 1885414 | 11/2012 |
| EP | 2526987 | 11/2012 |
| EP | 1885415 | 5/2013 |
| EP | 2586477 | 5/2013 |
| EP | 2586478 | 5/2013 |
| EP | 1861141 | 12/2013 |
| EP | 2722931 B1 | 4/2014 |
| EP | 2493533 | 2/2015 |
| EP | 2488232 | 1/2016 |
| EP | 3108914 | 12/2016 |
| EP | 3108914 A1 | 12/2016 |
| EP | 2913075 | 5/2017 |
| PL | 208660 B1 | 5/2011 |
| WO | 1991/14467 | 10/1991 |
| WO | 1999/38554 | 8/1999 |
| WO | 2002053214 | 7/2002 |
| WO | 2006045526 | 5/2006 |
| WO | 2006126902 | 11/2006 |
| WO | 2007063342 | 6/2007 |
| WO | 2008087071 | 7/2008 |
| WO | 2010089417 A2 | 8/2010 |
| WO | 2010089418 A2 | 8/2010 |
| WO | 2015197629 | 12/2015 |
| WO | 2016/016184 | 2/2016 |
| WO | 2016/041883 | 3/2016 |
| WO | 2016107790 | 7/2016 |
| WO | 2017134131 | 8/2017 |

* cited by examiner

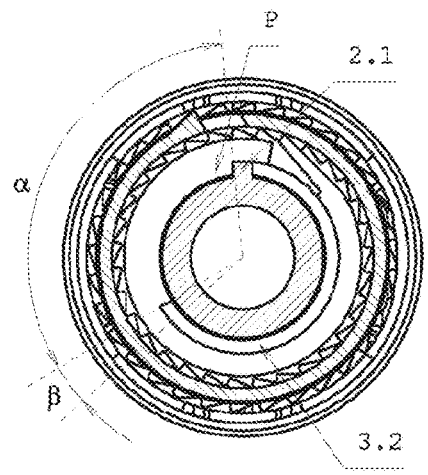
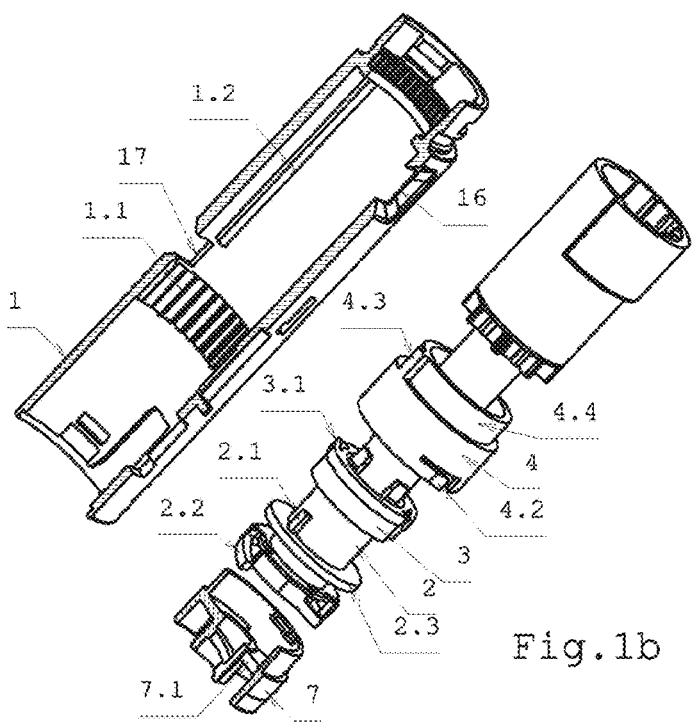
Fig.1a
Fig.1b
Fig.2a
Fig.2c
Fig.2b

CLUTCH ASSEMBLY WITH A BLOCKING SYSTEM FOR A MEDICAL INJECTION DEVICE

The invention concerns the field of medical devices for injecting pharmaceutical substances to a patient. In particular, the invention concerns a clutch with a blocking system that allows to block an injection device after the last dose has been delivered and an insufficient volume of the medicament remains in the device. The pharmaceutical substance may be any injectable pharmaceutical, e.g. insulin or growth hormone.

Clutch assemblies of the above described type are known in the art. An example of such a clutch is disclosed in the application EP16461534 in the name of the present applicant. In the device according to EP16461534 an arming mechanism is provided within a housing which is coupled with a pharmaceutical substance container. The arming mechanism comprises a setting sleeve which is axially non-displaceable and rotatable around the axis of the housing in two opposite directions by a defined setting angle. The setting sleeve is coupled with a spring which is strained by the rotation of the setting sleeve during arming of the device. Further, within the housing a dose delivery mechanism is also located, comprising a screw ring and a piston rod which is non-rotatable and axially displaceable within the setting sleeve, the piston rod cooperating with the screw ring so that during the arming of the device the screw ring and the piston rod are immobilized, and during delivery of each dose the piston rod is displaced along the housing by a defined distance due to unwinding of the spring and rotation of the screw ring. The displacement of the piston rod causes the fluid substance to be expelled from the reservoir. The device according to EP16461534 is also provided with blocking means preventing arming of the device for delivery of a subsequent dose after a defined number of doses of the substance have been delivered. The blocking means consist of protrusions located near the distal end of the setting sleeve on its inside surface, and longitudinal arms located at the proximal end of the piston rod.

Many known devices of the described type enable blocking of the device after delivery of the last full dose, when there is no enough medicament within the device for another full dose. This functionality ensures compliance with a design directive according to ISO Standard 11608-1:2014, point 5.5 k for fixed dose injection devices, according to which: "Fixed multi-dose NISs shall not allow pre-setting of the dose if a volume that is insufficient for the full fixed dose remains". However in such devices, without trying to pre-set a next dose, a user may only approximately assess (by the scale on the cartridge container) how much medicament is still left for delivery. A definite feed-back may only be obtained by trying to pre-set a next dose which is impossible to be pre-set.

The aim of the invention was to provide a clutch with a blocking system for a medical injection device that would be compliant with ISO Standard 11608-1:2014, point 5.5 k and that would enable a precise count of the delivered doses.

Another aim was to make the information about the number of the delivered and/or left to be delivered doses available to a user.

According to the invention a clutch assembly with a blocking system for a medical injection device is provided, the clutch assembly comprising a clutch sleeve located in a tubular housing, wherein the rotation of the clutch sleeve in a first direction arms the injection device for delivery of a defined dose of a medicament contained in a container and the rotation of the clutch sleeve in a second direction causes delivery of the dose.

The clutch assembly with a blocking system according to the invention is characterized in that:

a first ratchet sleeve is mounted on the clutch sleeve, the first ratchet sleeve being rotatable in two directions and cooperating with a second ratchet sleeve which is mounted on the first ratchet sleeve, the second ratchet sleeve being rotatable only in one direction, the housing has an internal toothed ring, the first ratchet sleeve has at least one ratchet, and the second ratchet sleeve has an internal toothed ring and at least one ratchet, the toothed rings have their teeth directed in mutually opposite directions and the ratchets are directed in mutually opposite directions, the at least one ratchet of the first ratchet sleeve cooperates with the toothed ring of the second ratchet sleeve, the at least one ratchet of the second ratchet sleeve cooperates with the toothed ring of the housing, wherein during arming of the device the first ratchet sleeve is stationary in relation to the second ratchet sleeve, the second ratchet sleeve turns in relation to the housing in said first direction by one tooth of the ring of the housing, and during delivery of a dose the second ratchet sleeve is stationary in relation to the housing while the first ratchet sleeve turns in relation to the second ratchet sleeve in said second direction by one tooth of the ring of the second ratchet sleeve, and wherein the second ratchet sleeve and the housing have blocking means for preventing the arming of the device when an insufficient volume of the medicament remains in the container, by blocking the rotation of the second ratchet sleeve in relation to the housing.

Preferably, the clutch sleeve and the first ratchet sleeve are provided with guiding means which during the rotation of the clutch sleeve by a first angle in both directions allow the rotation of the clutch sleeve in relation to the first ratchet sleeve, said first angle being less than 360 degrees.

Said guiding means may preferably be constituted by at least one rib formed on the outside of the clutch sleeve and at least one internally facing guiding projection of the first ratchet sleeve, the guiding projection defining at least one free space enabling the at least one rib to move within when the clutch sleeve rotates in relation to the first ratchet sleeve.

Said guiding means may also be constituted by at least one rib formed on the outside of the clutch sleeve and an end part of the first ratchet sleeve, the end part having a reduced diameter and having a recess defining at least one free space enabling the at least one rib to move within when the clutch sleeve rotates in relation to the first ratchet sleeve.

Preferably, each of the ratchet sleeves has two mutually opposite ratchets.

The clutch sleeve preferably has two mutually opposite ribs and the first ratchet sleeve preferably has two mutually opposite guiding projections defining two free spaces.

Said guiding means preferably allow the rotation of the clutch sleeve in relation to the first ratchet sleeve within said first angle, and their joint rotation within a second angle that is necessary to negotiate one tooth of the toothed rings, the sum of the first and second angle constituting the total angle required to arm the injection device.

Preferably, the means for blocking the rotation of the second ratchet sleeve in relation to the housing are constituted by a blocking projection on the inside of the housing for abutment with a projection located on the outside of the second ratchet sleeve.

The clutch sleeve, the first ratchet sleeve and the second ratchet sleeve preferably are non-translatable axially.

A scale may be printed on the outside surface of the second ratchet sleeve for indicating the number of delivered and/or left to be delivered doses of the medicament and the scale being visible to a user through a window in the housing.

The clutch with a blocking system according to the invention is advantageous in that its blocking system is able to precisely count the number of the delivered doses. Due to this, in a preferred embodiment of the invention, a user may see how many more doses are available before each arming of the device; this information may not be visible on a typical scale on the housing because of insufficient resolution. After the last full dose has been set and delivered, the injection device becomes blocked and may not be armed any more.

Preferred embodiments of the invention are shown on the appended drawing in which:

FIGS. 1a and 1b show perspective exploded views of the clutch with a blocking system according to the invention;

FIG. 2a shows a cross-section of the clutch of FIGS. 1a and 1b, along the plane A-A indicated in FIG. 3;

FIG. 2b shows a cross-section (analogous to that of FIG. 2a) of another embodiment of the clutch according to the invention;

FIG. 2c shows a partially sectional perspective view of another embodiment of the clutch according to the invention;

Figure 3:
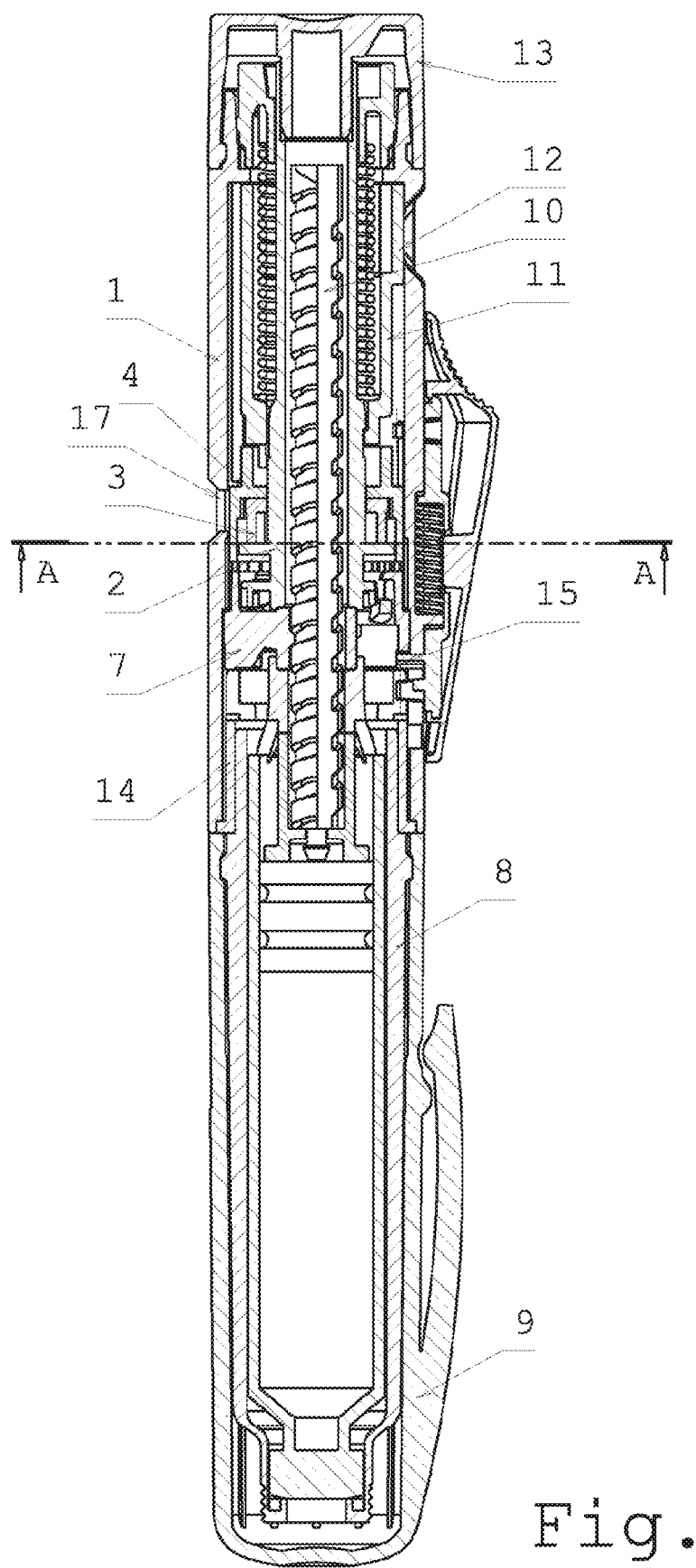
FIG. 3 shows a longitudinal section of an injection device provided with a clutch according to the invention.

FIG. 1a shows a sectional perspective view of the housing 1 of the clutch according to the invention. FIG. 1b shows other components of the clutch, removed from the housing 1. FIG. 1b shows that a first ratchet sleeve 3 and a second ratchet sleeve 4 are mounted on a clutch sleeve 2. The first ratchet sleeve 3 abuts a flange 2.3 located on the distal side of the clutch sleeve 2. The flange 2.3 constitutes a centering element for the second ratchet sleeve 4 and axially positions the system.

Below, the blocking system of the clutch will be described in detail. The blocking system blocks the injection device after the last full dose of a medicament has been delivered. The blocking system comprises said two ratchet sleeves 3 and 4 cooperating with each other as well as with the clutch sleeve 2 and the housing 1 in order to block the device against its arming for delivery of a next dose when a defined number of doses has already been delivered. The system may also serve to indicate the current state of the injection device (armed or not armed) and optionally to indicate the number of delivered and/or left to be delivered doses in the cartridge. The first ratchet sleeve 3 is rotatable in two directions while the second ratchet sleeve 4 is rotatable only in one direction. The clutch sleeve 2, the first ratchet sleeve 3 and the second ratchet sleeve 4 are axially non-translatable in relation to each other.

In the embodiment shown in FIGS. 1a and 2b the first ratchet sleeve 3 has two substantially peripheral resilient ratchets 3.1 for cooperation with the second ratchet sleeve 4. Further, the first ratchet sleeve 3 has two guiding projections 3.2 for cooperation with respective ribs 2.1 formed on the outside of the clutch sleeve 2. Between the guiding projections 3.2 two free spaces P are formed on both sides of said projections, the spaces P enabling the ribs 2.1 to move during the rotation of the first ratchet sleeve 3 in relation to the clutch sleeve 2. The cooperation of the ratchets 3.1 of the first ratchet sleeve 3 with the second ratchet sleeve 4 is possible due to a toothed ring 4.1 formed inside the second ratchet sleeve 4. The ratchets 3.1 engage the teeth of the toothed ring 4.1. The second ratchet sleeve 4 also has two resilient ratchets 4.2 for cooperation with the housing 1 inside which an internal toothed ring 1.1 is formed. The teeth of the rings 4.1 and 1.1 are directed in the mutually opposite directions. Similarly, the ratchets 3.1 and 4.2 are directed in the mutually opposite directions. An important feature of the second ratchet sleeve 4 is a projection 4.3 having a form of a blocking rib cooperating with a respective blocking projection 1.2 located on the inside of the housing 1.

The invention is not limited by the number of the resilient ratchets of both ratchet sleeves. For example, the clutch according to the invention may also be realized as shown in a cross-section of FIG. 2a, where the first ratchet sleeve 3 has only one substantially peripheral resilient ratchet 3.1 cooperating with the second ratchet sleeve 4 and the second ratchet sleeve 4 has also only one resilient ratchet 4.2 cooperating with the housing 1. The number of the ratchets may also be more than 2 (not shown in the figures).

In the embodiment shown in FIG. 2a the first ratchet sleeve 3 has also only one guiding projection 3.2 cooperating with just one rib 2.1 formed on the outside of the clutch sleeve 2. In this case only one free space P is formed for guiding the rib 2.1.

In the embodiment shown in FIG. 2c the guiding means consist of one rib 2.1 formed on the outside of the clutch sleeve 2, as in the embodiment of FIG. 2a, and the distal end part 3.3 of the first ratchet sleeve 3. The distal end part 3.3 has a reduced outside diameter in relation to the rest of the first ratchet sleeve 3 and it comprises a recess 3.4 defining a free space P. In this case the free space P enables the only one rib 2.1 to move within during the rotation of the clutch sleeve 2 in relation to the first ratchet sleeve 3.

The operation of the blocking system will be described with particular reference to FIG. 2b. FIG. 2b shows an exemplary system in which the ratchet sleeve 3 and the ratchet sleeve 4 each have two ratchets and there are two free spaces P between the two guiding projections 3.2. The angular extension of the free spaces defines a first angle $\alpha$ of 105 degrees. The teeth of the toothed rings 4.1 and 1.1 are angularly spaced by 11.5 degrees in this embodiment. Consequently, each toothed ring 4.1, 1.1 has 32 teeth in in this case; considering a dead zone of the second ratchet sleeve 4 (it may not make a full revolution because of the space occupied by the ribs 2.1), the injection device may deliver 30 doses. Obviously, the injection device may be designed to deliver a different number of doses; in such case the number of the teeth of the toothed rings and the angular space between them would be different. Also, the scope of free rotation of the clutch sleeve 2 defined by the space P would be different.

FIG. 2b shows the system when the injection device is not armed, i.e. before a dose has been pre-set. During a complete arming of the device (pre-setting of a dose) the clutch sleeve 2 is turned to the left by a total angle 120 degrees. Considering that the free spaces P between the guiding projections 3.2 extend through the first angle $\alpha$ of 105 degrees, when the clutch sleeve 2 is turned to the left by the 105 degrees, the ribs 2.1 first negotiate the free spaces P (during which the first ratchet sleeve 3 is not rotated). Then, the ribs 2.1 abut the projections 3.2 in consequence of which the clutch sleeve 2 and the first ratchet sleeve 3 rotate together through the next part of the rotation, i.e. a second angle $\beta$ of 15 degrees. This common rotation results in that the second ratchet sleeve 4 is turned by 15 degrees because during this rotation to the left the ratchets 3.1 press on the teeth of the ring 4.1. As the teeth of the ring 1.1 of the housing 1 are directed in the direction opposite to the teeth of the ring 4.1, and the respective ratchets are also directed in the opposite directions to each other, the rotation of the second ratchet sleeve 4 by 15 degrees results in that the ratchets 4.2 negotiate one tooth of the ring 1.1 (the teeth are spaced by 11.5 degrees). Upon the above described total rotation by the 120 degrees the phase of arming is concluded and the injection device is ready for delivery of a dose.

During the delivery of a dose the clutch sleeve 2 is turned back to the right by the first angle of 105 degrees and its ribs 2.1 negotiate again first the free spaces P. Turning the clutch sleeve 2 by further 15 degrees causes the ribs 2.1 to abut the projections 3.2 and press the first ratchet sleeve 3 so that the ratchets 3.1 negotiate one tooth of the toothed ring 4.1. Therefore, after the delivery of a dose (one complete cycle), i.e. when the clutch sleeve 2 has been turned back by a total angle of 120 degrees to the right, the first ratchet sleeve 3 has been turned to the right by one tooth of the toothed ring 4.1 and the second ratchet sleeve 4 has been turned to the left by one tooth of the toothed ring 1.1. The device is ready for a next cycle.

Rotation of the clutch sleeve 2 to the left, i.e. the arming of the injection device, may be repeated until the rib 4.3 meets the blocking projection 1.2 located within the housing 1 (FIGS. 1a and 1b). The rib 4.3 and the blocking projection 1.2 constitute means for blocking the injection device against being armed for delivery of a dose that would exceed the scope of operation of the device, i.e. in a situation where the amount of medicament remaining in the cartridge is insufficient. The rib 4.3 and the blocking projection 1.2 are positioned so as to enable rotation of the second ratchet sleeve 4 in relation to the housing 1 within a defined angle beyond which further rotation is not possible. Hence, the blocking projection 1.2 of the housing together with a scale sleeve 12, defines the scope of operation of the device.

In this embodiment the second ratchet sleeve 4 has a proximal part 4.4 having a smaller external diameter. On the part 4.4 the axially extending projection 4.3 is formed. It projects radially outside of the part 4.4. The longitudinal blocking projection 1.2 is formed inside the housing 1. Consequently, when the clutch sleeve 2 and the second ratchet sleeve 4 have been rotated by a defined angle, the projection 4.3 meets the blocking projection 1.2 and further rotation is not possible. In this situation the rotation by the full angle necessary for the arming of the device may not be performed because when the free space P (105 degrees) has been negotiated by the clutch sleeve 2, the second ratchet sleeve 4 may not be rotated further and it blocks the whole device.

In an injection device (see FIG. 3) having a delivery mechanism comprising a torsional spring 11 which is strained during arming of the device and released during delivery of a dose in order to make the clutch sleeve rotate (to the right in the described embodiment), the force of the driving spring 11 resets the device because the elastic ratchet arms 2.2 of the clutch sleeve 2 may not be positioned to engage the screw ring 7 during the arming of the device (see the description of FIG. 3 below).

FIG. 3 shows a longitudinal section of an injection device provided with a clutch with the last dose blocking system according to the invention.

It is a device for repeated delivery of a fixed dose of a medicament; in FIG. 3 it is shown in an armed state, i.e. ready for use and before delivery of a first dose. As shown in FIG. 3, the mechanisms of the device are located in the housing 1 connectable with a container 8 for a cartridge with the medicament, covered with a cap 9.

The mechanisms of the device include the clutch assembly with the blocking system and a delivery mechanism. The clutch assembly with the blocking system has been described above in detail with reference to FIGS. 1a, 1b and 2a, 2b, 2c.

The clutch sleeve 2 is mounted on a non-rotatable piston rod 10, which may only be translated distally. The driving spring 11 is mounted on the clutch sleeve 2 and a scale sleeve 12 is mounted on and surrounds the spring 11. Rotation of the clutch sleeve 2 is realized by means of a knob 13. The proximal end of the driving spring 11 is fixed within the housing 1 during assembly of the device and the distal end of the driving spring 11 is fixed to the clutch sleeve 2. Therefore, the rotation of the clutch sleeve 2 e.g. to the left by 120 degrees causes the driving spring 11 to become strained. When released, the driving spring 11 causes delivery of a dose.

The piston rod 10 has an external thread engaging an internal thread of the screw ring 7. The internal thread of the screw ring 7 is designed in such a way that rotation of the screw ring 7 by 120 degrees causes delivery of a required dose. The piston rod 10 has a non-circular cross-section and it has two longitudinal grooves on its external surface. The two grooves engage respective projections on a blocking sleeve 14 so that the piston rod 10 is blocked against rotation and during the rotation of the screw ring 7 the piston rod 10 is translated axially by a defined distance expelling the dose of the medicament.

The clutch sleeve 2 has three resilient arms 2.2 located at its distal end (in FIG. 2b only two of them a visible). The resiliency of the arms 2.2 allows them to be tilted axially. On the other hand, inside the screw ring 7 a peripheral ledge 7.1 is formed having an opening 7.2. Due to this arrangement, during the arming of the device, i.e. each time the clutch sleeve 2 is rotated by 120 degrees and the driving spring 11 is strained, one of the arms 2.2 falls into the opening 7.2 and engages the ledge 7.1 inside the screw ring 7. During the arming the screw ring 7 is blocked against rotation by a typical trigger 15 mounted on the housing 1. Upon release of the trigger 15, the screw ring 7 that is engaged with the clutch sleeve 2 by one of the arms 2.2, may rotate taking over the rotation of the clutch sleeve 2 which in turn is urged by the driving spring 11 which was strained during the arming when the screw ring was blocked.

The cooperation of the clutch sleeve 2 with the driving spring 11, the blocking sleeve 14 and the trigger 15, as well as the cooperation of the piston rod 10 with the blocking sleeve 14 are analogous as in the injection device described in EP16461534.

On the housing of the injection device a window 16 may be located allowing an indicator of the state of the device (armed/not armed) to be seen by a user, the indicator being placed on the scale sleeve.

An important advantage of the clutch assembly according to the invention is that the second ratchet sleeve 4 is rotated in the housing in one direction only, by one tooth of the toothed ring 1.1 each time the device is armed (a dose is pre-set). The second ratchet sleeve 4 never comes back to its initial position. Due to such arrangement the position of the second ratchet sleeve 4 in relation to the housing 1 unambiguously defines the number of the delivered doses and this information may be communicated to a user.

To this aim, a calibration visible through the housing 1 may be provided on the external surface of the second ratchet sleeve 4. The calibration may serve as indicator of the number of delivered doses or the number of doses that remain to be delivered. For example a window 17 may be made on the housing 1 disclosing said calibration. Other embodiments are possible, e.g. a transparent housing and corresponding markings of the second ratchet sleeve 4.

The invention claimed is:

1. A clutch assembly with a blocking system for a medical injection device, the clutch assembly comprising: a clutch sleeve located in a tubular housing, wherein the rotation of the clutch sleeve in a first direction arms the injection device for delivery of a defined dose of a medicament contained in a container and the rotation of the clutch sleeve in a second direction causes delivery of the dose, wherein a first ratchet sleeve is mounted on the clutch sleeve, the first ratchet sleeve being rotatable in two directions and cooperating with a second ratchet sleeve which is mounted on the first ratchet sleeve, the second ratchet sleeve being rotatable only in one direction, the housing has an internal toothed ring, the first ratchet sleeve has at least one ratchet, and the second ratchet sleeve has an internal toothed ring and at least one ratchet, the toothed rings have their teeth directed in mutually opposite directions and the ratchets are directed in mutually opposite directions, the at least one ratchet of the first ratchet sleeve cooperates with the toothed ring of the second ratchet sleeve, the at least one ratchet of the second ratchet sleeve cooperates with the toothed ring of the housing, wherein during arming of the device the first ratchet sleeve is stationary in relation to the second ratchet sleeve, the second ratchet sleeve is turned in relation to the housing in said first direction by one tooth of the ring, and during delivery of a dose the second ratchet sleeve is stationary in relation to the housing while the first ratchet sleeve is turned in relation to the second ratchet sleeve in said second direction by one tooth of the ring, and wherein the second ratchet sleeve and the housing have blocking means for preventing the arming of the device when an insufficient volume of the medicament remains in the container, by blocking the rotation of the second ratchet sleeve in relation to the housing.

2. The clutch assembly according to claim 1, wherein, the clutch sleeve and the first ratchet sleeve are provided with guiding means which during the rotation of the clutch sleeve by a first angle in both directions allow the rotation of the clutch sleeve in relation to the first ratchet sleeve, the first angle being less than 360 degrees.

3. The clutch assembly according to claim 2, wherein, said guiding means are constituted by at least one rib formed on the outside of the clutch sleeve and at least one internally facing guiding projection of the first ratchet sleeve, the guiding projection defining at least one free space enabling the at least one rib to move within when the clutch sleeve rotates in relation to the first ratchet sleeve.

4. The clutch assembly according to claim 2, wherein, said guiding means are constituted by at least one rib formed on the outside of the clutch sleeve and an end part of the first ratchet sleeve, the end part having a reduced diameter and having a recess defining at least one free space enabling the at least one rib to move within when the clutch sleeve rotates in relation to the first ratchet sleeve.

5. The clutch assembly according to claim 1, wherein, each of the ratchet sleeves has two mutually opposite ratchets respectively.

6. The clutch assembly according to claim 3, wherein, the clutch sleeve has two mutually opposite ribs and the first ratchet sleeve has two mutually opposite guiding projections defining two free spaces.

7. The clutch assembly according to claim 2, wherein, said guiding means allow the rotation of the clutch sleeve in relation to the first ratchet sleeve within said first angle and their joint rotation within a second angle that is necessary to negotiate one tooth of the toothed rings, the sum of the first and second angles constituting an angle required to arm the injection device.

8. The clutch assembly according to claim 1, wherein, the blocking means for blocking the rotation of the second ratchet sleeve in relation to the housing are constituted by a blocking projection on the inside of the housing for abutment with a projection located on the outside of the second ratchet sleeve.

9. The clutch assembly according to claim 1, wherein, the clutch sleeve, the first ratchet sleeve and the second ratchet sleeve are non-translatable axially.

10. The clutch assembly according to claim 1, wherein, a scale is printed on the outside surface of the second ratchet sleeve, the scale indicating a number of delivered and/or left to be delivered doses of the medicament and the scale being visible to a user through a window in the housing.

* * * * *